United States Patent
Farnan et al.

(10) Patent No.: US 7,931,663 B2
(45) Date of Patent: Apr. 26, 2011

(54) BALLOON CATHETER WITH NON-DEPLOYABLE STENT

(75) Inventors: Robert C. Farnan, Davie, FL (US); Dirk Voland Hoyns, Conyers, GA (US); Anand Ram, Lilburn, GA (US)

(73) Assignee: AngioScore, Inc., Fremont, CA (US)

( * ) Notice: Subject to any disclaimer, the term of this patent is extended or adjusted under 35 U.S.C. 154(b) by 1304 days.

(21) Appl. No.: 11/292,426

(22) Filed: Dec. 1, 2005

(65) Prior Publication Data

US 2006/0085025 A1    Apr. 20, 2006

Related U.S. Application Data

(63) Continuation of application No. 10/651,557, filed on Aug. 29, 2003, now abandoned, which is a continuation-in-part of application No. 10/399,589, filed as application No. PCT/US02/35547 on Nov. 6, 2002, now Pat. No. 7,691,119.

(60) Provisional application No. 60/344,982, filed on Nov. 9, 2001.

(51) Int. Cl.
*A61M 29/00* (2006.01)
(52) U.S. Cl. ..................... 606/194; 606/159
(58) Field of Classification Search ............... 623/1.11, 623/1.17; 606/191–195, 159; 604/96.01, 604/97.01, 103, 103.05, 103.09, 104, 509
See application file for complete search history.

(56) References Cited

U.S. PATENT DOCUMENTS

| | | | | |
|---|---|---|---|---|
| 2,701,559 A | * | 2/1955 | Cooper | 600/569 |
| 2,854,983 A | * | 10/1958 | Baskin | 604/103.11 |
| 4,637,396 A | * | 1/1987 | Cook | 606/194 |
| 4,723,549 A | * | 2/1988 | Wholey et al. | 606/194 |
| 4,921,484 A | * | 5/1990 | Hillstead | 604/104 |
| 4,950,227 A | * | 8/1990 | Savin et al. | 623/1.12 |
| 4,998,539 A | * | 3/1991 | Delsanti | 128/898 |
| 5,071,407 A | * | 12/1991 | Termin et al. | 604/104 |
| 5,102,417 A | * | 4/1992 | Palmaz | 606/195 |
| 5,108,416 A | | 4/1992 | Ryan et al. | |
| 5,176,693 A | * | 1/1993 | Pannek, Jr. | 606/159 |
| 5,190,058 A | * | 3/1993 | Jones et al. | 128/898 |
| 5,222,971 A | * | 6/1993 | Willard et al. | 606/198 |
| 5,449,372 A | * | 9/1995 | Schmaltz et al. | 606/198 |
| 5,449,373 A | * | 9/1995 | Pinchasik et al. | 606/198 |
| 5,456,667 A | * | 10/1995 | Ham et al. | 604/107 |
| 5,527,282 A | * | 6/1996 | Segal | 604/104 |
| 5,571,086 A | * | 11/1996 | Kaplan et al. | 604/96.01 |
| 5,607,442 A | | 3/1997 | Fischell et al. | |

(Continued)

FOREIGN PATENT DOCUMENTS

EP    1 179 323 A2    2/2002

(Continued)

*Primary Examiner* — Todd E Manahan
*Assistant Examiner* — Erin Colello
(74) *Attorney, Agent, or Firm* — Kilpatrick Townsend & Stockton LLP

(57) ABSTRACT

An angioplasty balloon including a non-deployable stent to prevent or reduce the potential for slippage of the inflated balloon with respect to the vessel wall being treated. The balloon includes a non-deployable stent that is adapted to be secured to the balloon or angioplasty balloon catheter. The stent has a proximal end, a distal end, and at least one extension section, at least one set of serpentine rings and at least one set of elongation links that allow expansion of the strut to accommodate the inflation of the balloon. The stent is made of a material so that the stent collapses upon deflation of the balloon.

12 Claims, 13 Drawing Sheets

U.S. PATENT DOCUMENTS

| | | | |
|---|---|---|---|
| 5,730,698 A * | 3/1998 | Fischell et al. .................... 600/3 |
| 5,755,708 A * | 5/1998 | Segal ............................ 604/107 |
| 5,755,781 A * | 5/1998 | Jayaraman ................... 623/1.16 |
| 5,766,238 A * | 6/1998 | Lau et al. ......................... 600/36 |
| 5,776,141 A * | 7/1998 | Klein et al. ................... 623/1.11 |
| 5,797,935 A * | 8/1998 | Barath .......................... 606/159 |
| 5,868,708 A * | 2/1999 | Hart et al. ...................... 604/104 |
| 5,868,779 A | 2/1999 | Ruiz |
| 5,904,698 A * | 5/1999 | Thomas et al. ............... 606/159 |
| 5,994,667 A | 11/1999 | Merdan et al. |
| 6,036,689 A * | 3/2000 | Tu et al. ........................... 606/41 |
| 6,053,913 A * | 4/2000 | Tu et al. ........................... 606/41 |
| 6,071,285 A | 6/2000 | Lashinski et al. |
| 6,071,286 A | 6/2000 | Mawad |
| 6,077,298 A * | 6/2000 | Tu et al. ....................... 623/1.19 |
| 6,106,548 A | 8/2000 | Roubin et al. |
| 6,117,104 A | 9/2000 | Fitz |
| 6,146,323 A * | 11/2000 | Fischell ............................ 600/3 |
| 6,152,944 A | 11/2000 | Holman et al. |
| 6,190,403 B1 * | 2/2001 | Fischell et al. .............. 623/1.16 |
| 6,203,569 B1 * | 3/2001 | Wijay .......................... 623/1.15 |
| 6,206,910 B1 | 3/2001 | Berry et al. |
| 6,245,040 B1 * | 6/2001 | Inderbitzen et al. ...... 604/103.07 |
| 6,258,087 B1 * | 7/2001 | Edwards et al. ................ 606/41 |
| 6,309,414 B1 * | 10/2001 | Rolando et al. ............. 623/1.15 |
| 6,312,459 B1 | 11/2001 | Huang et al. |
| 6,325,779 B1 | 12/2001 | Zedler |
| 6,325,813 B1 * | 12/2001 | Hektner ........................ 606/191 |
| 6,371,961 B1 | 4/2002 | Osborne et al. |
| 6,416,539 B1 * | 7/2002 | Hassdenteufel ............. 623/1.15 |
| 6,475,234 B1 | 11/2002 | Richter et al. |
| 6,475,236 B1 * | 11/2002 | Roubin et al. ............... 623/1.15 |
| 6,478,807 B1 * | 11/2002 | Foreman et al. ............. 606/194 |
| 6,540,722 B1 * | 4/2003 | Boyle et al. .................... 604/106 |
| 6,551,310 B1 * | 4/2003 | Ganz et al. ....................... 606/41 |
| 6,569,180 B1 | 5/2003 | Sirhan et al. |
| 6,605,107 B1 * | 8/2003 | Klein ........................... 623/1.11 |
| 6,613,072 B2 * | 9/2003 | Lau et al. ..................... 623/1.11 |
| 6,616,678 B2 * | 9/2003 | Nishtala et al. ............... 606/198 |
| 6,626,861 B1 * | 9/2003 | Hart et al. .................. 604/96.01 |
| 6,648,912 B2 | 11/2003 | Trout, III et al. |
| 6,656,351 B2 * | 12/2003 | Boyle ........................... 210/136 |
| 6,663,660 B2 * | 12/2003 | Dusbabek et al. ........... 623/1.11 |
| 6,695,813 B1 * | 2/2004 | Boyle et al. .................... 604/106 |
| 6,743,196 B2 * | 6/2004 | Barbut et al. .............. 604/101.01 |
| 6,840,950 B2 * | 1/2005 | Stanford et al. .............. 606/200 |
| 6,872,206 B2 * | 3/2005 | Edwards et al. ................ 606/41 |
| 7,186,237 B2 * | 3/2007 | Meyer et al. ............... 604/96.01 |
| 7,354,445 B2 * | 4/2008 | Nicholson et al. ........... 606/200 |
| 2001/0001823 A1 * | 5/2001 | Ryan .............................. 606/108 |
| 2001/0007082 A1 * | 7/2001 | Dusbabek et al. ........... 623/1.11 |
| 2001/0012950 A1 * | 8/2001 | Nishtala et al. ............... 606/198 |
| 2001/0016753 A1 * | 8/2001 | Caprio et al. ................. 606/192 |
| 2002/0038144 A1 | 3/2002 | Trout, III et al. |
| 2002/0045930 A1 * | 4/2002 | Burg et al. ................... 623/1.11 |
| 2002/0111633 A1 * | 8/2002 | Stoltze et al. ................. 606/108 |
| 2002/0165599 A1 | 11/2002 | Nasralla |
| 2003/0023200 A1 * | 1/2003 | Barbut et al. ..................... 604/9 |
| 2003/0028235 A1 * | 2/2003 | McIntosh et al. ............ 623/1.11 |
| 2003/0074046 A1 | 4/2003 | Richter |
| 2003/0105509 A1 | 6/2003 | Jang et al. |
| 2003/0149468 A1 | 8/2003 | Wallsten |
| 2003/0153870 A1 * | 8/2003 | Meyer et al. ............... 604/96.01 |
| 2003/0171799 A1 | 9/2003 | Lee et al. |
| 2003/0187494 A1 * | 10/2003 | Loaldi ......................... 623/1.11 |
| 2003/0195609 A1 | 10/2003 | Berenstein et al. |
| 2003/0199970 A1 * | 10/2003 | Shanley ....................... 623/1.16 |
| 2003/0199988 A1 | 10/2003 | Devonec et al. |
| 2003/0208244 A1 | 11/2003 | O'Shaughnessy et al. |
| 2004/0143287 A1 * | 7/2004 | Konstantino et al. ......... 606/194 |
| 2006/0149308 A1 | 7/2006 | Melsheimer et al. |
| 2006/0184191 A1 | 8/2006 | O'Brien |

FOREIGN PATENT DOCUMENTS

| WO | WO 98/05377 | 2/1998 |
| WO | WO 03/041760 A2 | 5/2003 |

* cited by examiner

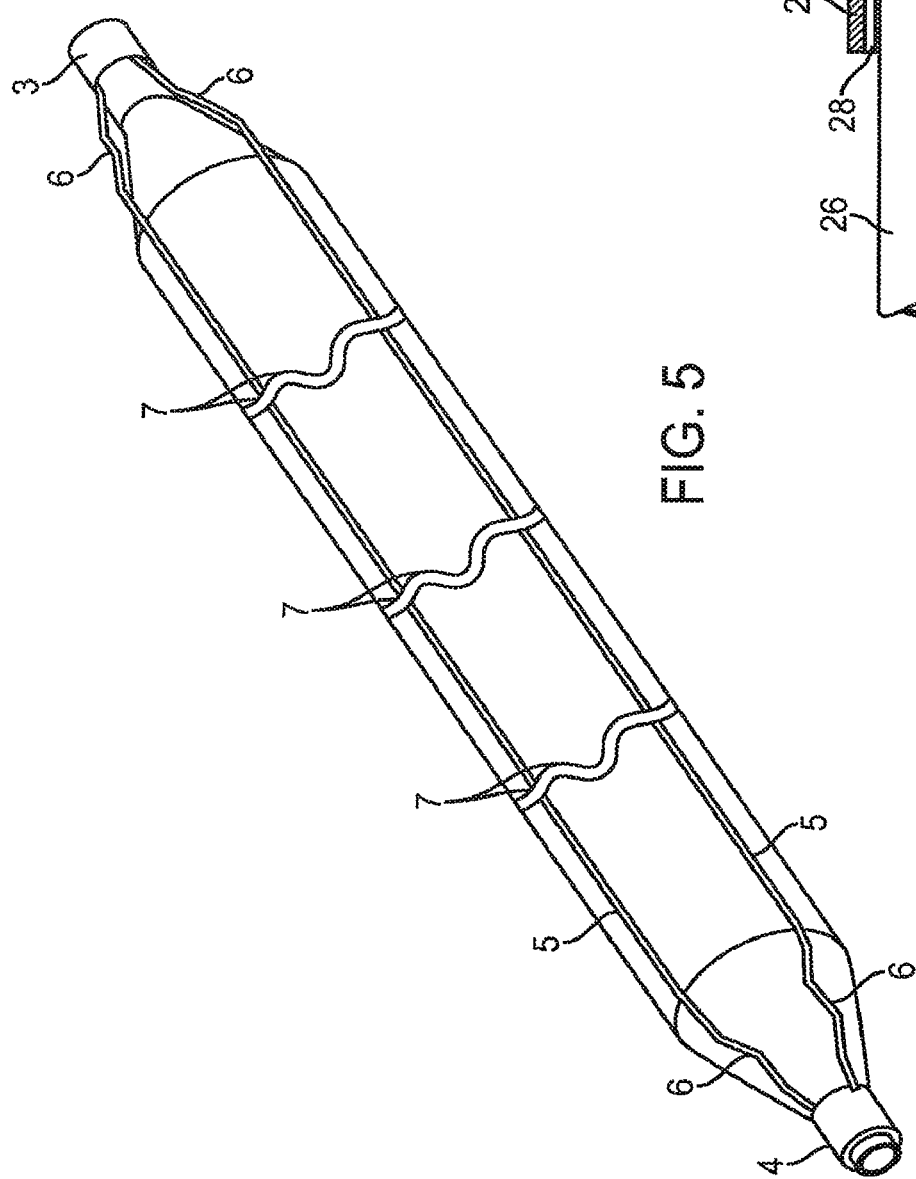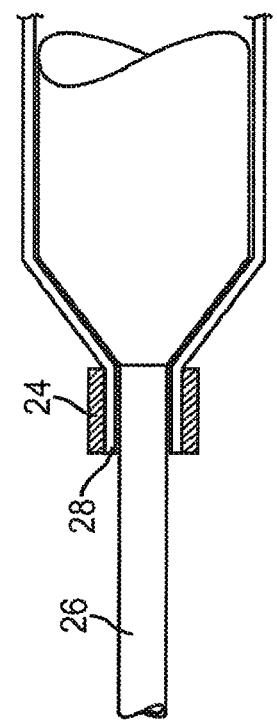

BALLOON CATHETER WITH NON-DEPLOYABLE STENT

CROSS-REFERENCES TO RELATED APPLICATIONS

This application is a continuation of U.S. patent application Ser. No. 10/651,557, filed Aug. 29, 2003, now abandoned which was a continuation-in-part of U.S. patent application Ser. No. 10/399,589, filed on Apr. 18, 2003, now U.S. Pat. No. 7,691,119, which is the U.S. National Stage of PCT Application No. PCT/US02/35547, filed Nov. 6, 2002, which claimed the benefit of U.S. Provisional No. 60/344,982, filed Nov. 9, 2001, the full disclosures of which are incorporated herein by reference.

BACKGROUND OF THE INVENTION

When a balloon used for percutaneous transluminal angioplasty (PTA) or percutaneous transluminal coronary angioplasty (PTCA) is inflated and forced into contact with the plaque, the balloon can have a tendency to move or slip longitudinally in relation to the lesion or the vessel wall being treated.

Cutting balloons (atherotomy) have recently shown clinical efficacy in preventing the reoccurrence of some types of restenosis (specifically calcified lesions and in-stent restenosis). The cutting balloon is a coronary dilatation catheter with 3 to 4 atherotomes (microsurgical blades) bonded longitudinally on the balloon surface. As the cutting balloon is inflated, the atherotomes move radially and open the occluded artery by incising and compressing the arterial plaque in a controlled manner. An additional advantage of the cutting balloon is that it maintains its position during inflation by using the metal blades on the external surface of the balloon to penetrate into the tissue and prevent the balloon from moving.

Accordingly, it is the principal objective of the present invention to provide a PTA or PTCA balloon that, like a cutting balloon, has a reduced potential of slippage when inflated in a vessel.

BRIEF DESCRIPTION OF THE DRAWINGS

FIG. 5 is a perspective view of an alternate embodiment of the non-deployable stent associated with an angioplasty balloon that has a longer working length than the angioplasty balloon shown in FIGS. 1 and 2.

FIG. 5A is a detailed cross-sectional view of one end of the stent of FIG. 5.

DETAILED DESCRIPTION OF THE INVENTION

Figure 1:
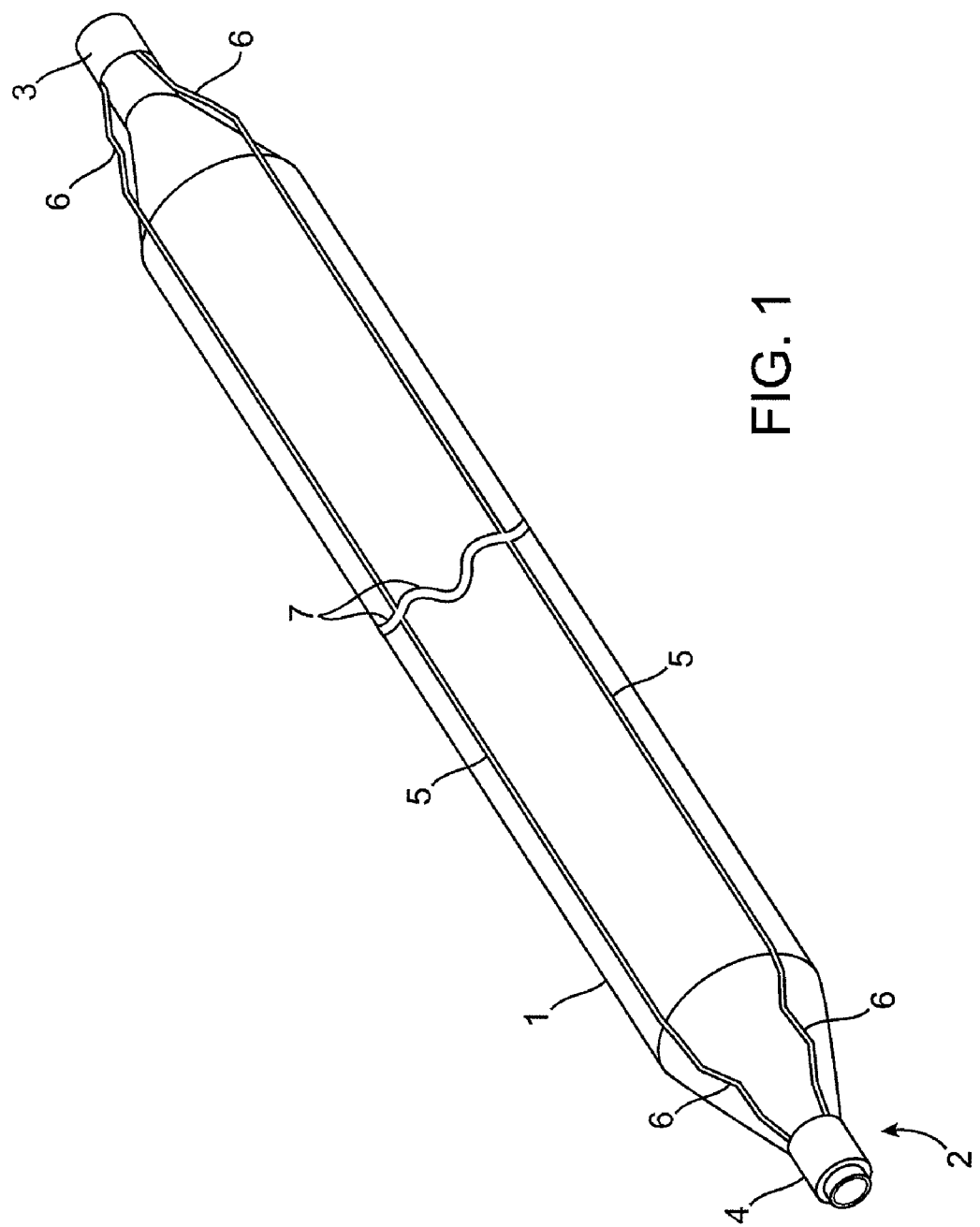
FIG. 1 is a perspective view of an inflated angioplasty balloon incorporating a non-deployable stent according to the present invention.
Figure 2:
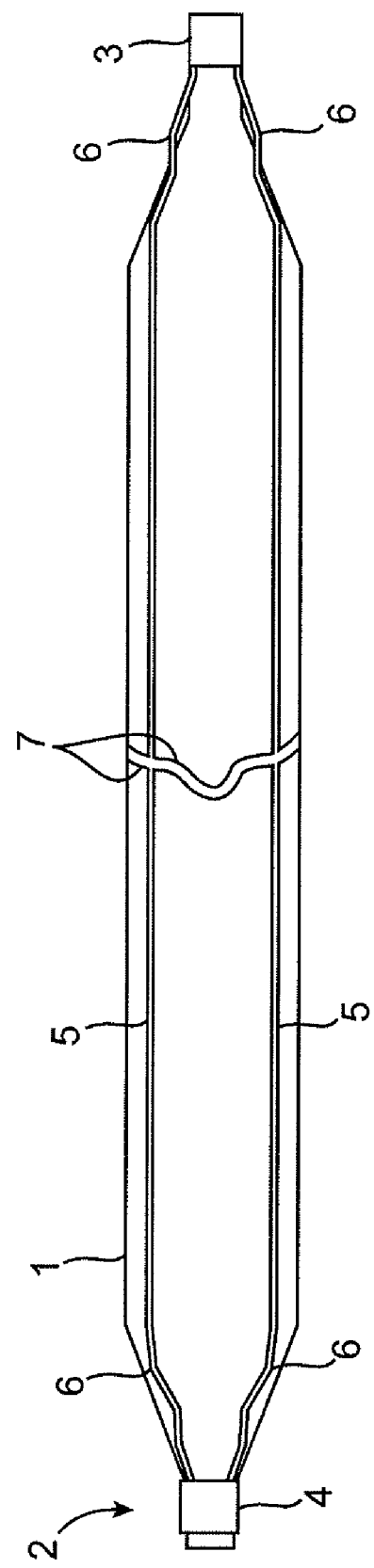
FIG. 2 is a plan view of the inflated angioplasty balloon and non-deployable stent of FIG. 1.

The non-deployable stent of the present invention may be used in conjunction with a conventional balloon catheter. A PTA or PTCA catheter (dilatation catheter) may be a coaxial catheter with inner and outer members comprising a guide wire lumen and a balloon inflation lumen, respectively. Each member can have up to 3 layers and can be reinforced with braids. The proximal end of the catheter has a luer hub a guidewire and for connecting an inflation means, and a strain relief tube extends distally a short distance from the luer hub. The distal ends of the outer and inner members may include a taper. The catheter shaft is built using conventional materials and processes. A catheter having multi-durometer tubing with variable stiffness technology is also a possibility. The catheter should be compatible with standard sheaths and guide catheters which are well known in the art. Optionally, the catheter may be a multi-lumen design.

The balloon 1 may be made of either nylon or nylon copolymer (compliant, non-puncture) or PET (high pressure, non-compliant) with a urethane, polymer, or other material and coating known in the art to provide tackiness and/or puncture resistance. The balloon may be a multi-layered balloon with a non-compliant inner layer to a most compliant outer layer or multilayered with similar material. For example, a inner most layer of PET, which provides a higher pressure balloon, surrounded by an outer layer of nylon, which provides a more puncture-resistant surface. The balloon may be from 1.5-12 mm in diameter (1.5-4 mm for coronary and 4-12 mm for peripheral vessels) and 15-60 mm in length (5-40 mm for coronary and up to 60 mm for peripheral vessels). The balloon inflation rated pressure will be from 8-20 atmospheres, depending on the wall thickness of the balloon. When inflated, the balloon ends or necks are cone-shaped.

In keeping with the invention, the balloon is provided with a Nitinol (NiTi) or another material such as for example liquid metal, stainless steel, or other similar material, structure, generally designated 2, that incorporates bends for both radial and longitudinal expansion of the Nitinol structure 2 in response to longitudinal and radial expansion of the balloon during inflation, so that the Nitinol structure 2 maintains the balloon in its intended position during inflation. This Nitinol structure 2 can be described as a non-deployable or temporary stent that provides for both controlled cracking of vessel occlusion and gripping of vessel wall during an angioplasty procedure. The Nitinol structure 2 comprises a laser cut hypo tube that expands upon inflation of the balloon, but collapses upon deflation of the balloon because of the super-elastic properties of the Nitinol material, rather than remain expanded in the deployed condition, as would stents in general.

The Nitinol structure or non-deployable stent 2 has a proximal end 3, a distal end 4, and, therebetween, anywhere from 3-12 struts or wires 5 (depending on balloon size—but most likely 3-4 struts) with a pattern of radial and longitudinal bends. The use of laser cutting in connection with stent manufacture is well known (See, e.g., Meridan et al. U.S. Pat. No. 5,994,667), as is the use of the super-elastic nickel-titanium alloy Nitinol (see e.g., Huang et al. U.S. Pat. No. 6,312,459).

As seen in FIGS. 1-4, each end of the four struts 5 has a sinusoidal type bend 6 that allows the laser cut hypo tube to expand longitudinally when the balloon 1 is inflated. The linear length of the sinusoidal type bends 6 is sized to accommodate the longitudinal expansion of the balloon 1 due to inflation. The strut or wire 5 cross sectional shape can be round, triangular, elliptical, oval, or rectangular. Preferred thickness of the struts 5 ranges from 0.003 to 0.010 inch.

Figure 3:
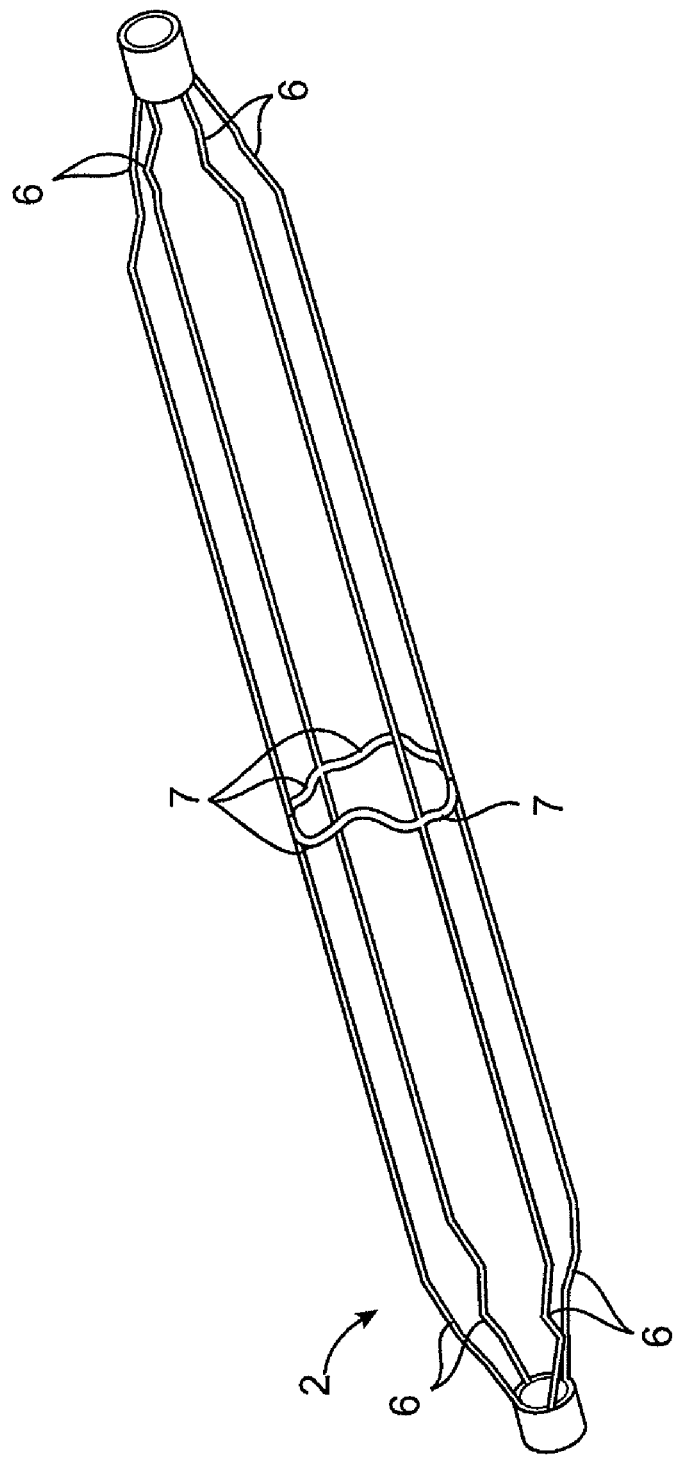
FIG. 3 is a perspective view of the non-deployable stent in its expanded condition, as shown in FIG. 1, with the angioplasty balloon removed so as to more clearly show the stent.
Figure 4:
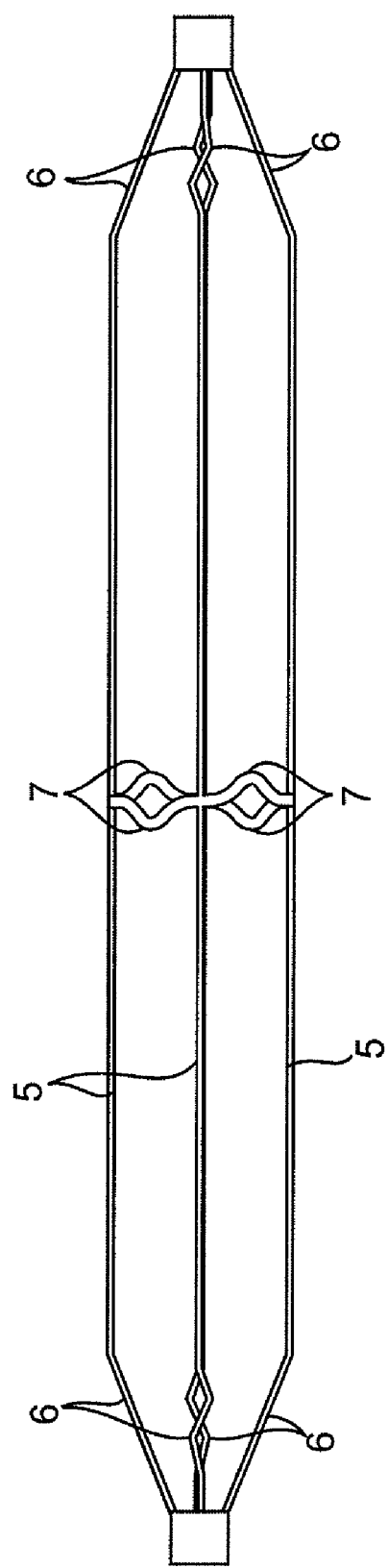
FIG. 4 is a plan view of the non-deployable stent of FIG. 3.

At the longitudinal center of the hypo tube, a U-shaped circumferential connector 7 joins each strut 5 to its adjacent strut. As best seen in FIGS. 3 and 4, the U-shaped connectors 7 are on opposing sides of the central radial axis. The distal end 4 of the hypo tube is adhered to the distal neck of the balloon or the distal end of the catheter shaft, and the proximal end 3 of the hypo tube is either attached to the proximal neck of the balloon or to the proximal end of the catheter shaft. The struts 5 may be attached to the working region of the balloon 1 to assist the hypo tube in staying with the balloon as it inflates and deflates.

Catheter shafts to which the balloon and laser cut hypo tube are attached can have diameters ranging from 2.5 F to 8 F, and the distal end may be tapered and slightly less in diameter than the proximal end.

Figure 6:
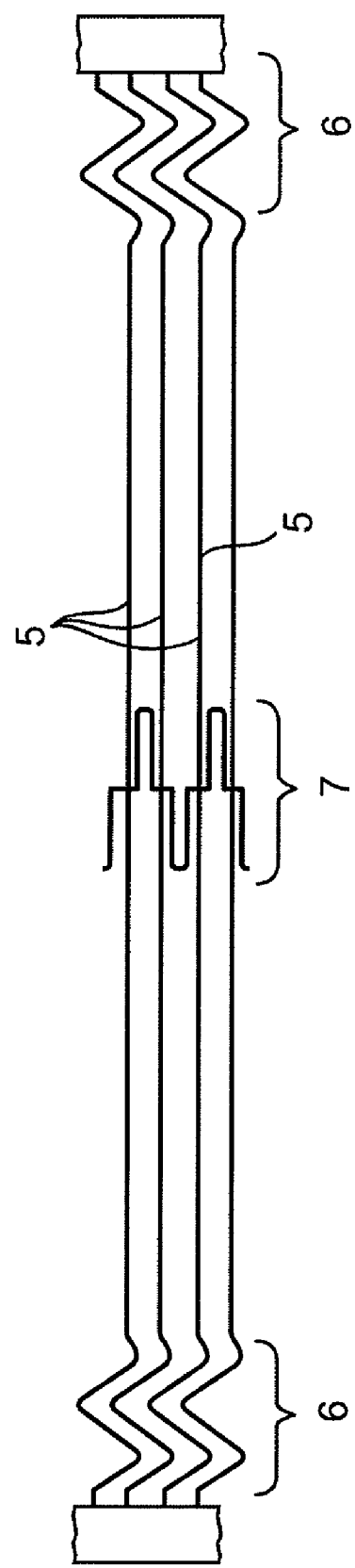
FIG. 6 is an engineering drawing showing, in plan view, the layout of a non-deployable stent adapted to be used with an angioplasty balloon of 20 mm in length. (All dimensions shown in the drawing are in inches.)

In FIG. 6, the dimensions of the laser cut hypo tube are for use with a 3 mm (0.118 in) diameter by 20 mm length balloon. The circumference of a 3 mm balloon is .PI.D=3.14(3 mm)=9.42 mm or 0.37 in. As can be readily appreciated, the total length of all U-shaped connectors 7 (up and back) must be greater than the circumference of the inflated balloon 1. The length of each U-shaped connector 7 (up and back), may be calculated using the following equation:

$$\frac{\pi d}{n},$$

where d is the diameter of the inflated balloon and n is the number of struts. The total length of the U-shaped bends (up and back) must exceed this length.

The resulting number is divided by 2 to get the length which each up-and-back side of the U-shaped connector should exceed. For example: for a 3 mm balloon compatible, laser-cut hypo tube with four struts, the length of each U-shaped connector (up and back) is 0.37 inch divided by 4=0.0925 in. Further divide by 2 and to get 0.04625 in. This is the length that each side of the U-shaped connector must exceed.

Figure 7:
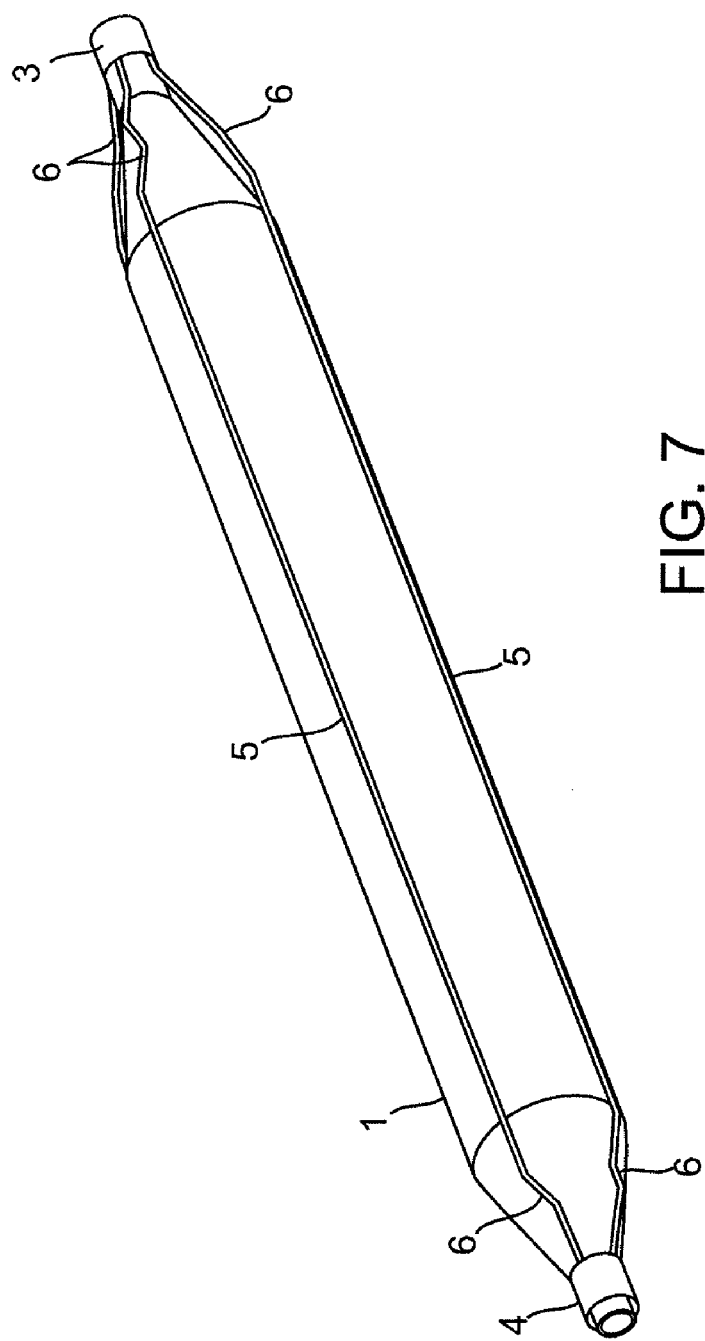
FIG. 7 is a perspective view of an inflated angioplasty balloon incorporating an alternative embodiment of a non-deployable stent which does not include any connecting elements between the struts intermediate the ends of the balloon.
Figure 8:
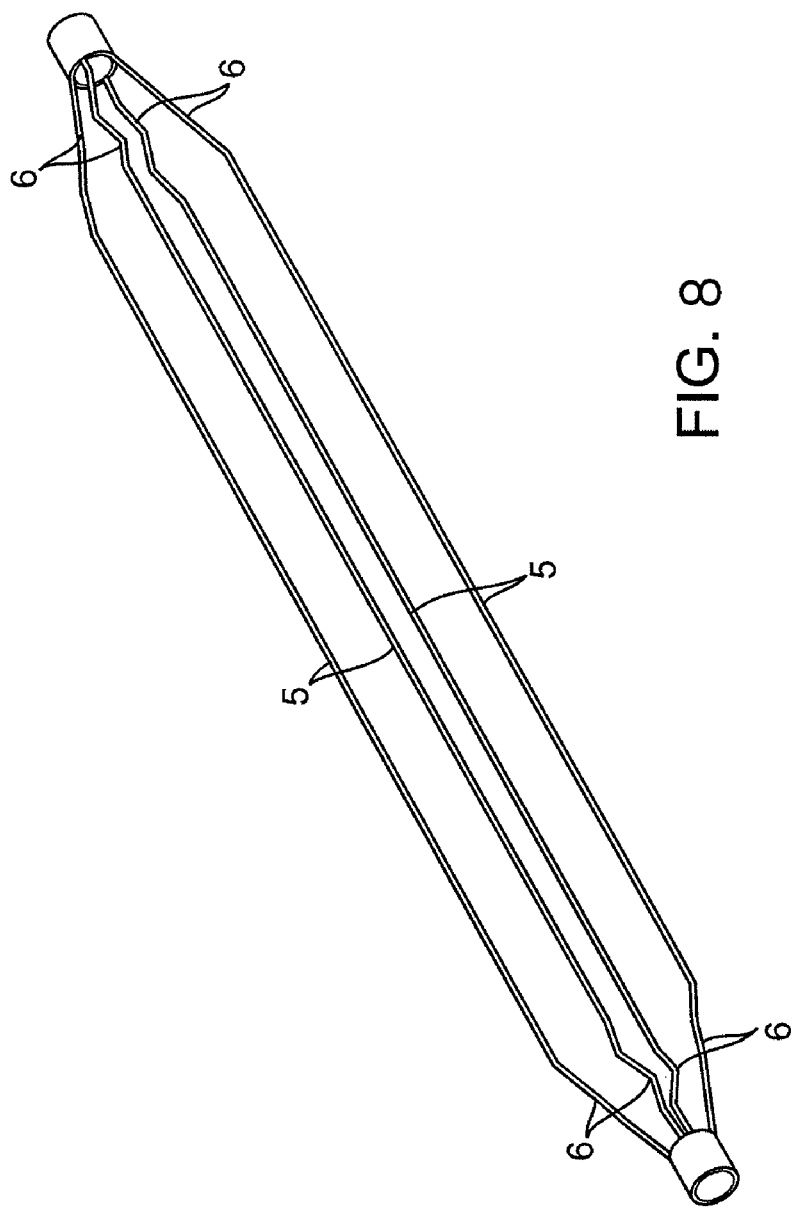
FIG. 8 is a perspective view of the non-deployable stent shown in FIG. 7, with the angioplasty balloon removed so as to more clearly show the stent.
Figure 9:
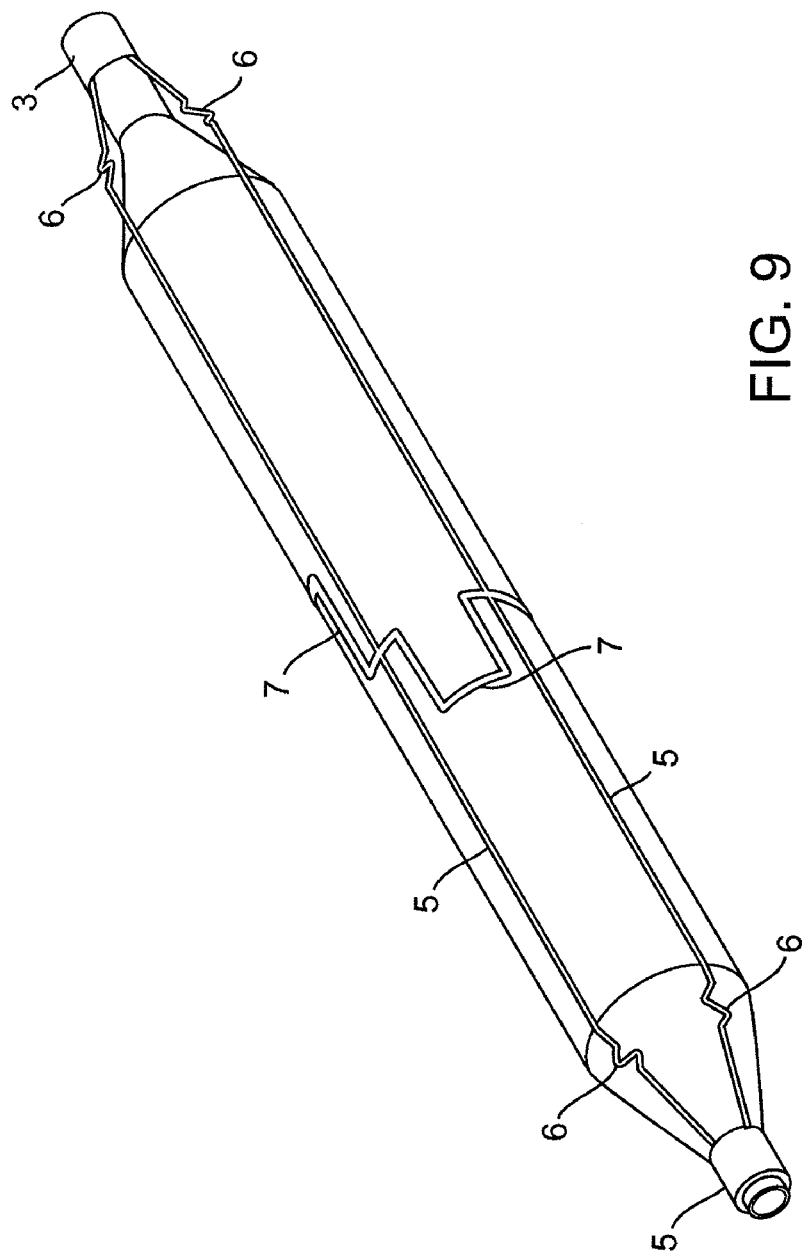
FIGS. 9 and 10 are perspective views similar to FIGS. 1, 5, and 7 showing a further embodiment of the invention.
Figure 10:
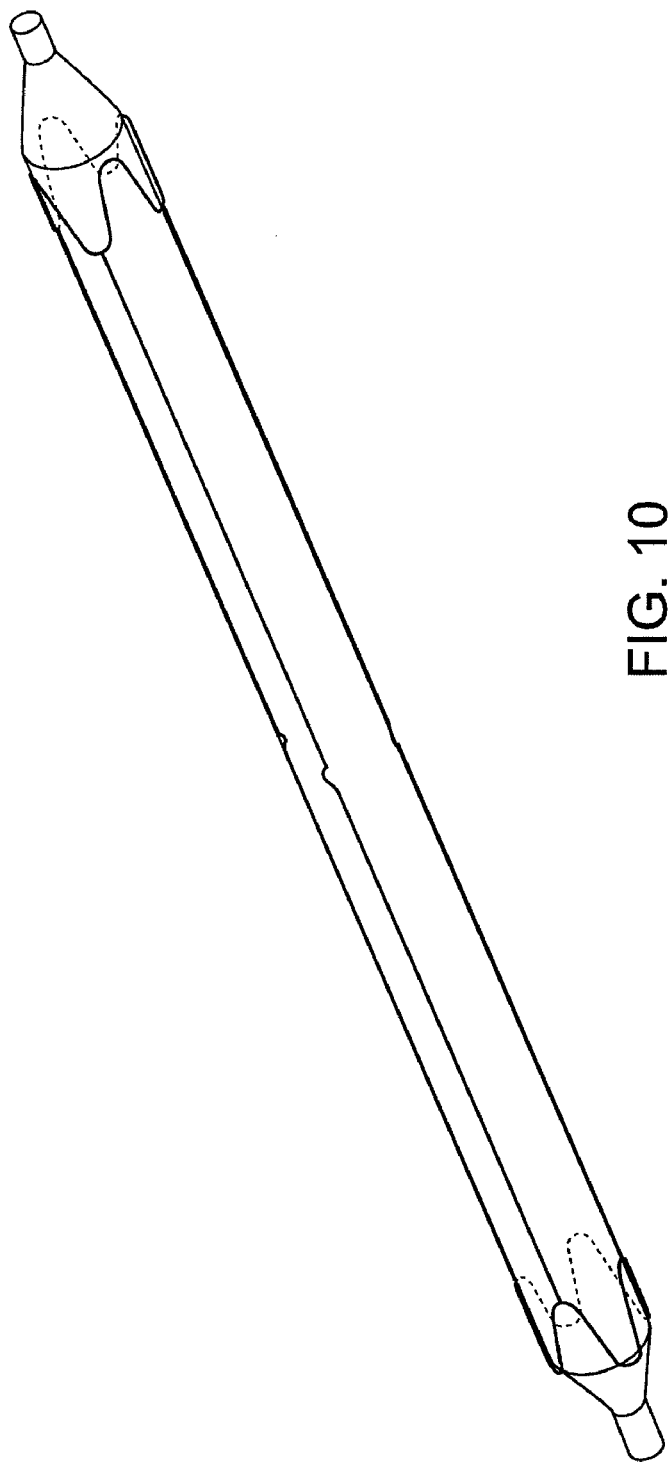
Figure 11:
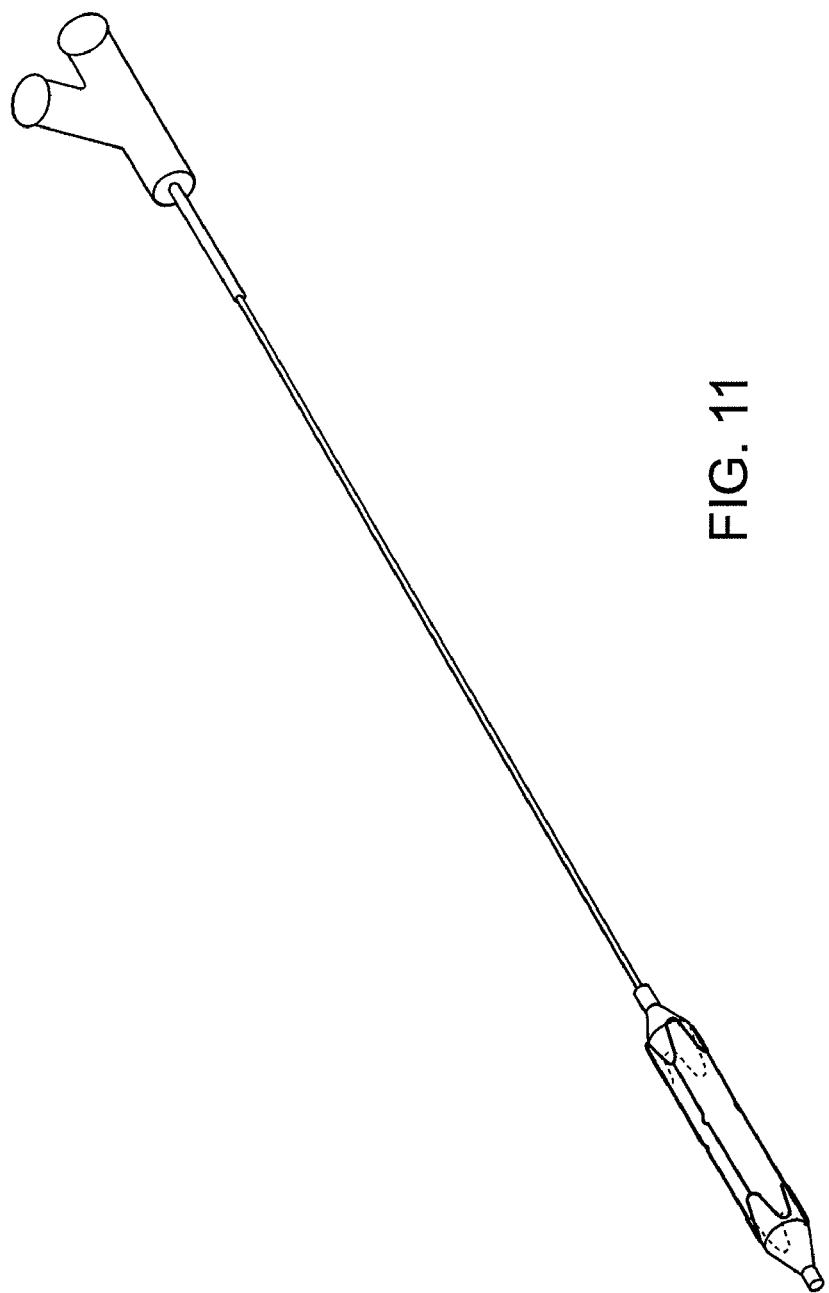
FIG. 11 is a perspective view of a further embodiment of the present invention showing the balloon and non-deployable stent in conjunction with a catheter.

There is also one or more sets of U-shaped connectors 7 in between the sinusoidal bends 6. The set includes one U-shaped connector for each strut (3 struts—a set of 3 U-shaped connectors; 4 struts—a set of 4 U-shaped connector; and so on). The number of U-shaped connector sets depends on the length of the balloon and thus, the length of the laser cut hypo tube. For a 20 mm length balloon, there is one set of U-shaped connectors spaced 10 mm from the end (at the halfway point along length of balloon). For a 40 mm length balloon, there are three sets of U-shaped connectors spaced in 10 mm increments (the first set is spaced 10 mm from one end; the second set is spaced 10 mm from first set; and the third set is spaced 10 mm from each the second set and the other end). The equation for number of sets of U-shaped connectors.

$$\frac{L-1}{10}$$

where L=length of balloon in mm. Other embodiments, such as those shown in FIGS. 7 and 8, do not incorporate the intermediate U-shaped connectors.

Figure 12:
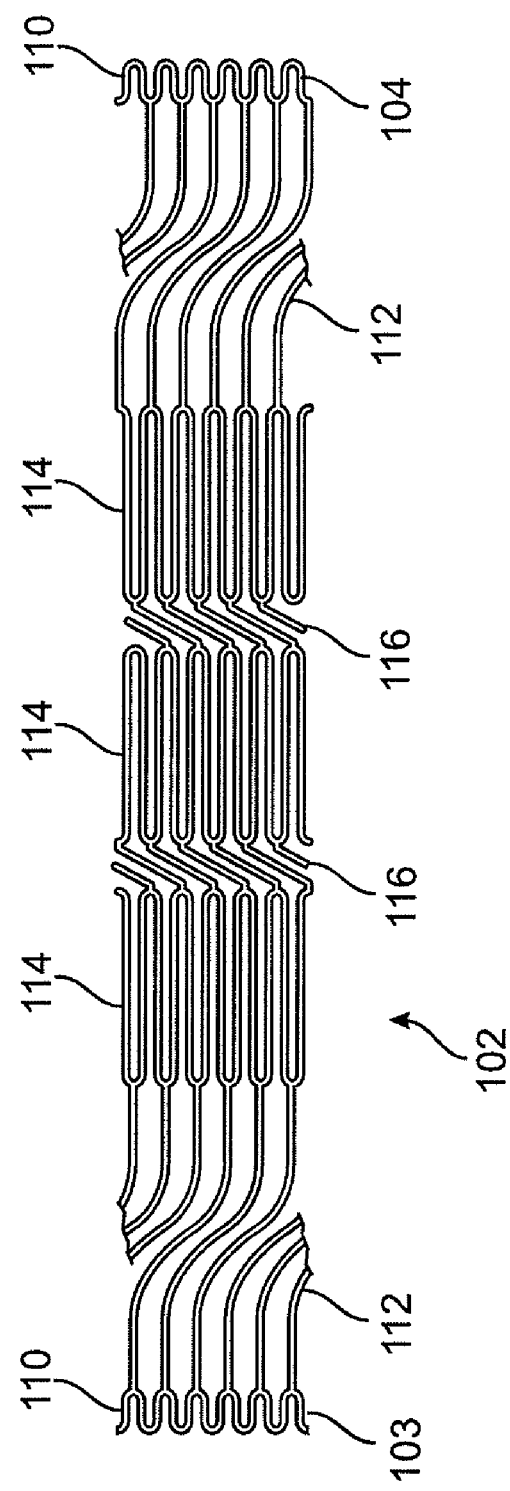
FIG. 12 is an engineering drawing showing, in plan view, the layout of another embodiment of a non-deployable stent adapted to be used with an angioplasty balloon, in accordance with the present invention.

FIG. 12 is directed to another embodiment of a non-deployable stent 102 which can be used with a conventional balloon catheter, in accordance with the present invention. The stent of this embodiment preferably has a Nitinol structure, though other materials can be used as discussed supra, that incorporates bends for both radial and longitudinal expansion of the stent in response to radial and longitudinal expansion of the balloon during inflation, so that the stent 102 maintains the balloon in its intended position. Similar to the stents of the other embodiments of the present invention discussed supra, the stent comprises a laser cut hypo tube that expands upon inflation of the balloon and collapses upon deflation of the balloon. Further, the stent is preferably secured to the balloon with some type of anchoring means. Preferably, such anchoring means are utilized at the ends of the stent and around the neck of the balloon. Examples of such anchoring means include an adhesive such as for example a UV adhesive, cyanoacrylate, or a two-part epoxy, RF heat welding, solvent bonding, or crimping or swaging the ends of the stent to the shaft. Alternatively, a mechanical anchoring means can be used to anchor the stent to the balloon. With such a means, a small sleeve 24 made of a similar material as the shaft 26 of the catheter is mounted over the ends 28 of the stent 30 and heat welded together where the ends of the stent are sandwiched between the shaft and the sleeve (FIG. 5A).

FIG. 12 shows the hypo tube of the stent in an unrolled (flat) and non-extended state. The stent 102 has a proximal end 103 and a distal end 104. At each end, there are cage mounted flanges 110. These flanges can be used to attach the stent to the neck of the balloon. The flanges also spring open radially to permit insertion of the balloon during assembly. Between the ends, the stent 102 includes extension sections 112, serpentine rings 114 and elongation links 116.

Serpentine rings 114 have a serpentine shape and allow the stent 102 to expand radially when a balloon in the stent is inflated. However, as the balloon expands, the serpentine rings 114 will shorten in length. Accordingly, extension sections 112 and elongation links 116 expand longitudinally to compensate for any shortening of the length of serpentine rings 114. Preferably, elongation links 116 have a z-shape, s-shape or accordion shape, as shown in FIG. 12.

Figure 13:
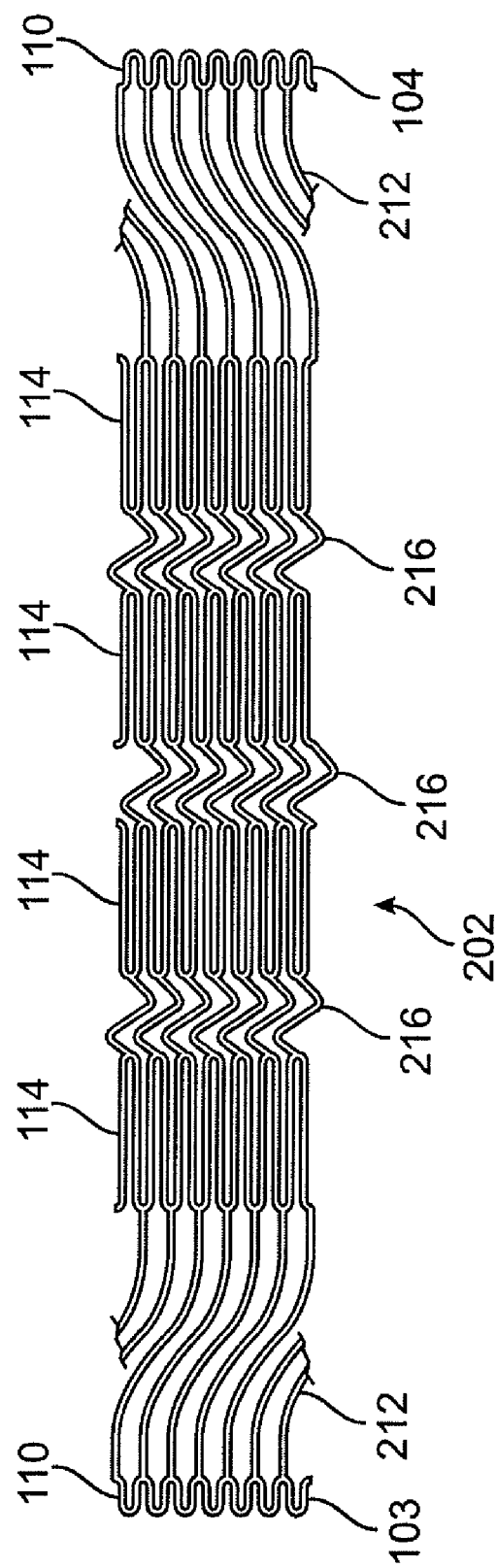
FIG. 13 an engineering drawing showing, in plan view, the layout of an alternate non-deployable stent of the embodiment of FIG. 12.

FIG. 13 is an alternative embodiment showing a stent 202 having the same features as the stent in FIG. 12 except that stent 202 in FIG. 13 has elongated links 216 with a different pattern than the elongated links 116 in stent 102 of FIG. 12. More specifically, elongated links 216 have a zig zag pattern. Stent 202 of FIG. 13 operates in a substantially similar manner to that of stent 102 in FIG. 12.

While the present invention is not limited in the number of serpentine rings, extension sections and elongated links used in the stent, FIG. 13 illustrates a preferred embodiment. The stent 202 in FIG. 13 has from proximal end 103 to distal end 104, a first extension section 112, a first set of serpentine rings 114, a first set of elongated links 216, a second set of serpentine rings 114, a second set of elongated links 216, a third set of serpentine rings 114, a third set of elongated links 216, a fourth set of serpentine rings 114, and a second extension section 112.

FIG. 13 also shows an example of possible dimensions, in inches, of each of the components of the stent 202. These dimensions would also be used for each of the similar components in stent 102 in FIG. 12.

It will be understood that the embodiments and examples of the present invention, which have been described, are illustrative of some of the applications of the principles of the present invention. Numerous modifications may be made by those skilled in the art without departing from the true spirit and scope of the invention.

What is claimed is:

1. A method for performing angioplasty in a blood vessel, said method comprising:
   introducing a balloon catheter into a blood vessel, said catheter having a shaft and an inflatable balloon;
   inflating the balloon to radially expand a non-deployable stent, wherein a central portion of the stent shortens in length as the stent is radially expanded, wherein the non-deployable stent includes (1) ends which are sandwiched between a sleeve and the shaft of the balloon catheter and (2) a region which expands longitudinally to compensate for foreshortening of the length which results from radial expansion; and
   deflating the balloon to allow the non-deployable stent to collapse over the balloon as it deflates.

2. A method as in claim 1, wherein the non-deployable stent comprises two ends attached to the shaft of the balloon catheter, one end being attached on each side of the balloon.

3. A method as in claim 2, wherein said region that expands includes at least one extension section between the end and the central section.

4. A method as in claim 3, wherein said region that expands includes a second extension section between the other end and the central section.

5. A method as in claim 2, wherein the non-deployable stent includes one or more elongation links along a length of the central section.

6. A method as in claim 1, wherein the central section of the non-deployable stent comprises a plurality of serpentine rings.

7. An angioplasty catheter comprising:
   a catheter shaft having a distal end and proximal end;
   an inflatable balloon disposed near the distal end of the catheter shaft;
   a non-deployable stent disposed over the inflatable balloon, said stent including a central section which radially expands and axially foreshortens when the balloon is inflated, an end, and an extension section between the end and the central section;
   wherein the end of the stent is sandwiched between a sleeve and the shaft on at least one side of the balloon and wherein the extension section of the stent longitudinally expands to accommodate axial shortening of the central section of the stent upon radial expansion of the stent resulting from balloon expansion.

8. An angioplasty catheter as in claim 7, wherein the stent includes a second end which is sandwiched between a sleeve and the catheter shaft on another side of the balloon.

9. An angioplasty catheter as in claim 8, the stent further comprises a second extension section between the second end and the central section of the stent.

10. An angioplasty catheter as in claim 9, wherein the central section comprises a plurality of axially joined serpentine rings.

11. An angioplasty catheter as in claim 8, further comprising at least one elongation link between adjacent serpentine rings in the central section of the stent.

12. An angioplasty catheter as in claim 11, including a plurality of elongation links between adjacent serpentine rings in the central section of the stent.

* * * * *